US012778622B2

(12) United States Patent
Jang et al.

(10) Patent No.: US 12,778,622 B2
(45) Date of Patent: Nov. 3, 2026

(54) MAGNETIC ROBOT

(71) Applicant: IUCF-HYU (INDUSTRY-UNIVERSITY COOPERATION FOUNDATION HANYANG UNIVERSITY), Seoul (KR)

(72) Inventors: Gun Hee Jang, Seoul (KR); Jun Chi Sa, Seoul (KR); Ji Min Park, Seoul (KR); Jun Hyoung Kwon, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 108 days.

(21) Appl. No.: 18/854,289

(22) PCT Filed: Mar. 2, 2023

(86) PCT No.: PCT/KR2023/002887
§ 371 (c)(1),
(2) Date: Oct. 4, 2024

(87) PCT Pub. No.: WO2023/167517
PCT Pub. Date: Sep. 7, 2023

(65) Prior Publication Data

US 2025/0241673 A1 Jul. 31, 2025

(30) Foreign Application Priority Data

Mar. 4, 2022 (KR) ........................ 10-2022-0027983

(51) Int. Cl.
*A61B 17/3207* (2006.01)
*A61B 17/00* (2006.01)

(52) U.S. Cl.
CPC ................ *A61B 17/320758* (2013.01); *A61B 2017/00876* (2013.01)

(58) Field of Classification Search
CPC ........ A61B 17/3207; A61B 17/320758; A61B 2017/00292; A61B 2017/00411;
(Continued)

(56) References Cited

U.S. PATENT DOCUMENTS 3,674,014 A * 7/1972 Tillander ............. A61B 1/0055 600/11
2008/0312578 A1* 12/2008 DeFonzo .......... A61M 25/0032 604/6.16
(Continued)

FOREIGN PATENT DOCUMENTS

JP 2021-137459 A 9/2021
KR 10-2016-0100853 A 8/2016
(Continued)

OTHER PUBLICATIONS

International Search Report of PCT/KR2023/002887 dated Jun. 7, 2023 [PCT/ISA/210].
(Continued)

*Primary Examiner* — Mohamed G Gabr
(74) *Attorney, Agent, or Firm* — Sughrue Mion, PLLC

(57) ABSTRACT

The present invention relates to a magnetic robot. The magnetic robot according to one embodiment of the present invention comprises: a body; and a work member which is connected to the body so as to be positioned in an anterior region of the body, and which is provided to be rotatable around a longitudinal center as an axis, wherein the body comprises: a housing part provided to have a preset length in the forward-backward direction so as to form an inner space; and a connection part positioned at a front end portion of the housing part so as to be provided to protrude toward
(Continued)

the longitudinal central axis of the housing part, and thus has a connection hole formed at the inner center thereof, and the work member comprises: a body part which is provided to have a preset length in the forward-backward direction, and which has at least one region provided as a magnetic body; and a fastening part provided to extend backward from the rear end of the body part so as to be inserted into the connection hole.

4 Claims, 6 Drawing Sheets

(58) Field of Classification Search
CPC A61B 2017/00876; A61B 2017/00477; A61B 2017/00345; A61B 2017/22094; A61B 2034/301; A61B 2090/035; A61B 2217/005; A61B 2217/007; A61B 34/73
See application file for complete search history.

(56) References Cited

U.S. PATENT DOCUMENTS

| | | | | |
|---|---|---|---|---|
| 2009/0306651 | A1* | 12/2009 | Schneider .............. | A61B 5/287 606/41 |
| 2014/0100646 | A1 | 4/2014 | Hassan et al. | |
| 2016/0235491 | A1* | 8/2016 | Choi ...................... | A61B 34/30 |

FOREIGN PATENT DOCUMENTS

| | | | |
|---|---|---|---|
| KR | 10-1659367 | B1 | 9/2016 |
| KR | 10-2019-0135330 | A | 12/2019 |
| KR | 10-2021-0012852 | A | 2/2021 |
| KR | 10-2021-0098200 | A | 8/2021 |
| KR | 10-2021-0098301 | A | 8/2021 |

OTHER PUBLICATIONS

Written Opinion of PCT/KR2023/002887 dated Jun. 7, 2023 [PCT/ISA/237].

* cited by examiner

MAGNETIC ROBOT

CROSS REFERENCE TO RELATED APPLICATIONS

This application is a National Stage of International Application No. PCT/KR2023/002887 filed on Mar. 2, 2023, claiming priority based on Korean Patent Application No. 10-2022-0027983 filed on Mar. 4, 2022.

TECHNICAL FIELD

The present invention relates to a magnetic robot, and more particularly, to a magnetic robot capable of moving in a blood vessel while effectively steering a front region of the magnetic robot, and effectively fragmenting and removing a thrombus through a drilling work.

BACKGROUND ART

Magnetic catheters are driven with a magnetic torque and a magnetic force by an external magnetic field generated by a magnetic driving system, and the magnetic catheters may be precisely controlled remotely, so that the magnetic catheters are being applied to many regions, and research and development on the magnetic catheters are being conducted.

A representative example is a magnetic catheter applied to a treatment of cardiac arrhythmia, and a blood vessel treatment magnetic catheter for a blood vessel treatment is being developed. In a case of the blood vessel treatment magnetic catheter, it is very important to perform a tunneling treatment function to unclog a solidly clogged blood vessel. Existing magnetic catheters perform a tunneling treatment by rotating a drill tip and allowing a person to push the magnetic catheter outside a body by using a hand or a linear slide mechanism.

Such magnetic catheters have a limitation in that when a lesion is positioned after a complex blood vessel, a force may not reach an end of the catheter so that the tunneling treatment may not be effectively performed.

DISCLOSURE

Technical Problem

An object of the present invention is to provide a magnetic robot capable of moving in a blood vessel while effectively steering a front region of the magnetic robot, and effectively fragmenting and removing a thrombus through a drilling work.

In addition, an object of the present invention is to provide a magnetic robot capable of adjusting a posture such that a longitudinal direction of a work member is inclined with respect to a longitudinal direction of a body.

In addition, an object of the present invention is to provide a magnetic robot capable of adjusting a position of a work member in a forward-rearward direction with respect to a body.

Technical Solution

According to one aspect of the present invention, there is provided a magnetic robot including: a body; and a work member connected to the body so as to be positioned in an anterior region of the body, and provided to be rotatable about a longitudinal center of the work member, wherein the body includes: a housing part having a preset length in a forward-rearward direction so as to form an inner space; and a connection part positioned at a front end portion of the housing part so as to protrude toward a longitudinal central axis of the housing part, and having a connection hole formed at an inner center of the connection part, and the work member includes: a body part having a preset length in the forward-rearward direction, and having at least one region provided with a magnetic body; and a fastening part extending rearward from a rear end of the body part so as to be inserted into the connection hole.

In addition, the work member may further include: a separation prevention part coupled to a rear end of the fastening part so as to be positioned in the inner space of the housing part, and having at least a partial region in which a section of the partial region, which is perpendicular to a longitudinal direction of the work member, is larger than an area of the connection hole.

In addition, a section of the connection hole, which is perpendicular to a longitudinal direction of the connection hole, may have a circular shape, a section of the fastening part, which is perpendicular to a longitudinal direction of the fastening part, may have a circular shape, and a diameter of the fastening part may be smaller than a diameter of a central region of the connection hole by a preset length.

In addition, a diameter of the connection hole may be larger in a front end portion of the connection part than in a longitudinal central region of the connection part.

In addition, the front end portion of the connection part may have a structure that widens outward from a rear side to a front side.

In addition, a diameter of the connection hole may be larger in a rear end portion of the connection part than in a longitudinal central region of the connection part.

In addition, the rear end portion of the connection part may have a structure that widens outward from a front side to a rear side.

In addition, at least one communication hole may be formed at an outer circumference of the housing part.

In addition, the communication hole may be inclined forward at a preset angle from the inner space to an outside.

Advantageous Effects

According to one embodiment of the present invention, a magnetic robot capable of moving in a blood vessel while effectively steering a front region of the magnetic robot, and effectively fragmenting and removing a thrombus through a drilling work can be provided.

In addition, according to one embodiment of the present invention, a magnetic robot capable of adjusting a posture such that a longitudinal direction of a work member is inclined with respect to a longitudinal direction of a body can be provided.

In addition, according to one embodiment of the present invention, a magnetic robot capable of adjusting a position of a work member in a forward-rearward direction with respect to a body can be provided.

BEST MODE

Figure 1:
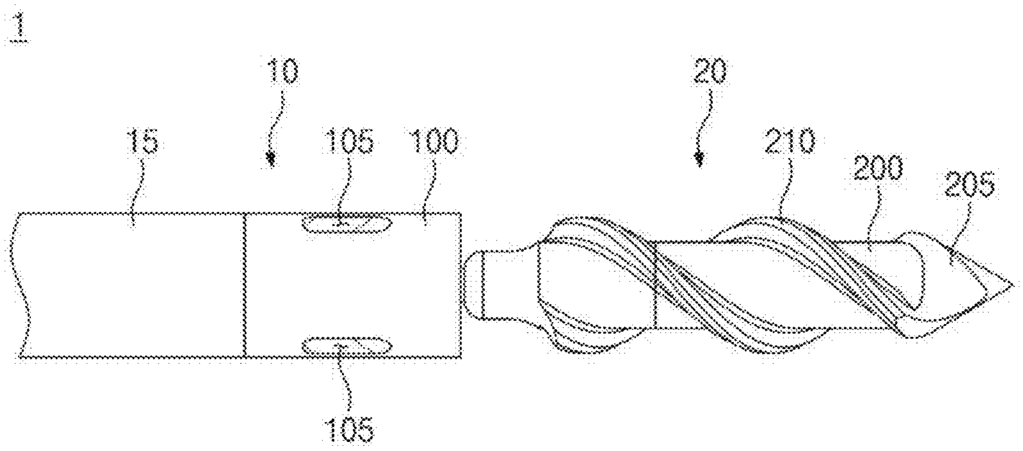
FIG. 1 is a view showing a magnetic robot according to one embodiment of the present invention.

According to one embodiment of the present invention, a magnetic robot includes: a body; and a work member connected to the body so as to be positioned in an anterior region of the body, and provided to be rotatable about a longitudinal center of the work member, wherein the body includes: a housing part having a preset length in a forward-rearward direction so as to form an inner space; and a connection part positioned at a front end portion of the housing part so as to protrude toward a longitudinal central axis of the housing part, and having a connection hole formed at an inner center of the connection part, and the work member includes: a body part having a preset length in the forward-rearward direction, and having at least one region provided with a magnetic body; and a fastening part extending rearward from a rear end of the body part so as to be inserted into the connection hole.

MODE FOR INVENTION

Hereinafter, exemplary embodiments of the present invention will be described in detail with reference to the accompanying drawings. However, the technical idea of the present invention is not limited to the embodiments described herein, but may be embodied in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, thicknesses of films and regions are exaggerated for effective description of the technical contents.

In addition, although the terms such as first, second, and third have been used to describe various elements in various embodiments of the present disclosure, the elements are not limited by the terms. The terms are used only to distinguish one element from another element. Therefore, an element mentioned as a first element in one embodiment may be mentioned as a second element in another embodiment. The embodiments described and illustrated herein include their complementary embodiments, respectively. Further, the term “and/or” used in the present disclosure is used to include at least one of the elements enumerated before and after the term.

As used herein, an expression in a singular form includes a meaning of a plural form unless the context clearly indicates otherwise. Further, the terms such as “including” and “having” are intended to designate the presence of features, numbers, steps, elements, or combinations thereof described herein, and shall not be construed to preclude any possibility of the presence or addition of one or more other features, numbers, steps, elements, or combinations thereof. In addition, the term “connection” used herein is used to include both indirect and direct connections of a plurality of elements.

Further, in the following description of the present detailed descriptions of known functions or invention, configurations incorporated herein will be omitted when they may make the gist of the present invention unnecessarily unclear.

Figure 2:
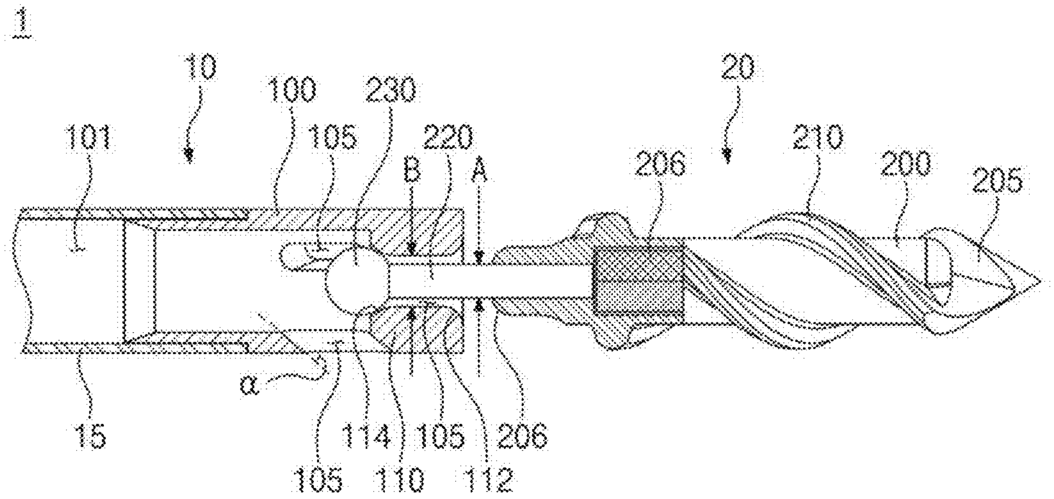
FIG. 2 is a view showing a section of one portion of the magnetic robot according to one embodiment of the present invention.

FIG. 1 is a view showing a magnetic robot according to one embodiment of the present invention, and FIG. 2 is a view showing a section of one portion of the magnetic robot according to one embodiment of the present invention.

Referring to FIGS. 1 and 2, according to one embodiment of the present invention, a magnetic robot 1 may include a body 10 and a work member 20.

According to one embodiment of the present invention, the magnetic robot 1 may be inserted into a blood vessel of a living body to remove foreign substances such as a thrombus. Hereinafter, regarding a direction in which the body 10 and the work member 20 are connected to each other, a direction in which the work member 20 is positioned will be defined as a front side, and a direction in which the body 10 is positioned will be defined as a rear side.

The body 10 may include a housing part 100 and a connection part 110.

The housing part 100 may have a preset length in a forward-rearward direction so as to form an inner space 101. An outer circumference of the housing part 100, which is perpendicular to a longitudinal direction of the housing part 100, may have a shape such as a circular shape or a polygonal shape. The inner space 101 of the housing part 100 may be opened rearward. When the magnetic robot 1 is used, a tube 15 may be connected to a posterior region of the housing part 100. At least one communication hole 105 may be formed at the outer circumference of the housing part 100. The communication hole 105 may be inclined forward at a preset angle α from the inner space to an outside. The communication hole 105 may have a preset length in a direction intersecting a circumferential direction of the housing part 100. For example, the communication hole 105 may have a preset length in the forward-rearward direction.

The connection part 110 may be positioned at a front end portion of the housing part 100 so as to protrude toward a longitudinal central axis of the housing part 100. Surfaces of the connection part 110, which face each other in a direction perpendicular to the longitudinal direction of the housing part 100, may be spaced apart from each other by a preset length, and a connection hole 115 may be formed at an inner center of the connection part 110. A section of the connection hole 115, which is perpendicular to a longitudinal direction of the connection hole 115, may have a circular shape. The connection hole 115 may have a preset length in the forward-rearward direction. A diameter of the connection hole 115 may be larger in a front end portion 112 of the connection part 110 than in a longitudinal central region of the connection part 110. For example, the front end portion 112 of the connection part 110 may have a structure that widens outward from a rear side to a front side. In addition, the front end portion 112 of the connection part 110 may have a structure that widens outward while being rounded with a preset curvature. A diameter of the connection hole 115 may be larger in a rear end portion 114 of the connection part 110 than in a longitudinal central region of the connection part 110. For example, the rear end portion 114 of the connection part 110 may have a structure that widens outward from a front side to a rear side. In addition, the rear end portion 114 of the connection part 110 may have a structure that widens outward while being rounded with a preset curvature.

The work member 20 may be connected to the body 10 so as to be positioned in an anterior region of the body 10. The work member 20 may have a preset length, and may be provided to be rotatable about a longitudinal center of the work member 20 so as to perform a function of removing a thrombus or the like attached to an inner side of a blood vessel. The work member 20 may include a body part 200, a fastening part 220, and a separation prevention part 230.

The body part 200 may have a preset length in the forward-rearward direction. An outer circumference of the body part 200, which is perpendicular to a longitudinal direction of the body part 200, may have a circular shape or the like. A blade 210 may be wound in a spiral shape around the outer circumference of the body part 200. A pointed portion 205 that is pointed forward may be formed at a front end of the body part 200. A rear end portion 206 of the body part 200 may be rounded. In addition, an outer circumference of the rear end portion 206 of the body part 200, which is perpendicular to a longitudinal direction of the rear end portion 206 of the body part 200, may have a circular shape, so that at least a portion of the rear end portion 206 of the body part 200 may inserted into the front end portion 112 of the connection part 110. At least one region of the body part 200 may be provided with a magnetic body 206. For example, the magnetic body 206 may be accommodated inside the body part 200. The magnetic body 206 may have N and S poles arranged in a direction orthogonal to the longitudinal direction of the body part 200. Accordingly, when a magnetic field is applied from the outside, a force may be generated in the magnetic body 206 so that the work member 20 may move inside the blood vessel while performing a drilling motion. In this case, a torque generated through the region in the magnetic body 206 may be expressed as Mathematical Formula 1.

$$T_e = m \times B_e \quad \text{[Mathematical Formula 1]}$$

(magnetic field: Be, Te: torque, m: magnetic moment of magnetic body)

In addition, in order to generate the drilling motion, the magnetic field may be applied in the following form.

$$B_e(t) = B_0(\cos(2\pi ft)U + \sin(2\pi ft)N \times U) \quad \text{[Mathematical Formula 2]}$$

($B_0$: intensity of magnetic field, f: rotation frequency, N: unit vector of rotation axis, U: unit vector perpendicular to rotation axis)

The fastening part 220 may extend rearward from a rear end of the body part 200 so as to be inserted into the connection hole 115. A section of the fastening part 220, which is perpendicular to a longitudinal direction of the fastening part 220, may have a circular shape. A diameter A of the fastening part 220 may be smaller than a diameter B of a central region of the connection hole 115 by a preset length. In this case, a difference between the diameter A of the fastening part 220 and the diameter B of the central region of the connection hole 115 may be clearly distinguished from an assembly tolerance that is generally considered upon designing mechanical elements for mutual assembly of the mechanical elements, and may refer to a value that is larger than the assembly tolerance. Accordingly, when a longitudinal central axis of the fastening part 220 and a longitudinal central axis of the connection hole 115 are aligned to overlap each other, an outer surface of the fastening part 220 may be spaced apart from the connection hole 115. A length of the fastening part 220 may be longer than a length of the central region of the connection hole 115. The length of the fastening part 220 may be longer than a length of the connection hole 115.

The separation prevention part 230 may be coupled to a rear end of the fastening part 220 so as to be positioned in the inner space of the housing part 100. At least a partial region of the separation prevention part 230 may be configured such that a section of the partial region, which is perpendicular to a longitudinal direction of the work member 20, may be larger than an area of the connection hole 115, thereby preventing the fastening part 220 from being separated through the connection hole 115. A front end portion of the separation prevention part 230 may widen outward while being rounded from a front side to a rear side. For example, the separation prevention part 230 may have a ball shape.

Figure 3:
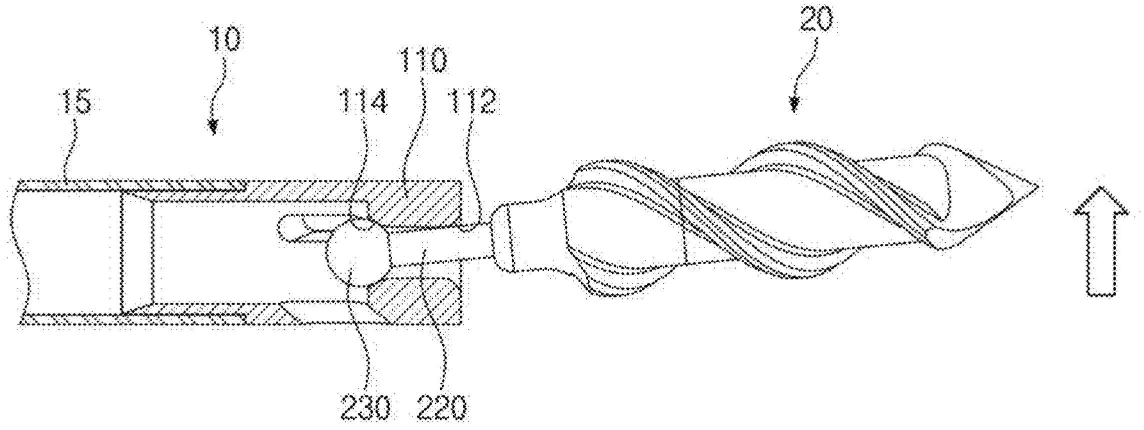
FIGS. 3 and 4 are views showing states where a direction in which a work member faces is adjusted.
Figure 4:
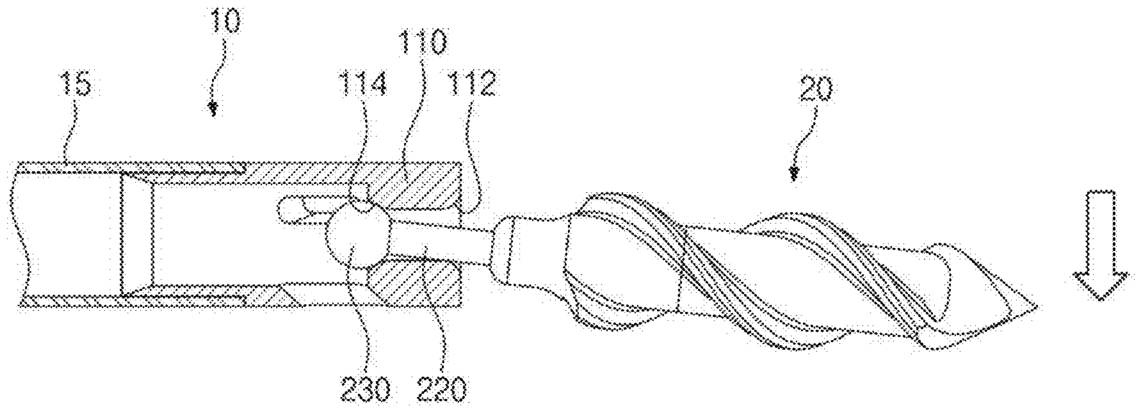

FIGS. 3 and 4 are views showing states where a direction in which a work member faces is adjusted.

Referring to FIGS. 3 and 4, a posture of the work member 20 may be adjusted such that the longitudinal direction of the work member 20 may be inclined with respect to a longitudinal direction of the body 10. For example, when an angle of the magnetic field applied to the work member 20 with respect to the longitudinal direction of the body 10 is adjusted, a direction in which the longitudinal direction of the work member 20 faces may be adjusted by a force generated by the magnetic field. In this case, when the longitudinal central axis of the fastening part 220 and the longitudinal central axis of the connection hole 115 are aligned to overlap each other, the outer surface of the fastening part 220 may be spaced apart from the connection hole 115, so that the posture of the work member 20 may be adjusted until a front end portion of the fastening part 220 and a rear end portion (or deviation prevention part) of the fastening part 220 make contact with the connection hole 115 in opposite directions. In addition, the front end portion 112 and the rear end portion 114 of the connection part 110 are may be rounded, so that even when the posture of the work member 20 is adjusted to allow the fastening part 220 or the separation prevention portion 230 to make contact with the connection part 110, damage caused by the contact may be prevented. Accordingly, according to the magnetic robot 1 of one embodiment of the present invention, steering ability may be improved by adjusting a direction of the work member 20 with respect to the body 10 during a process of moving forward after being inserted into the blood vessel.

Figure 5:
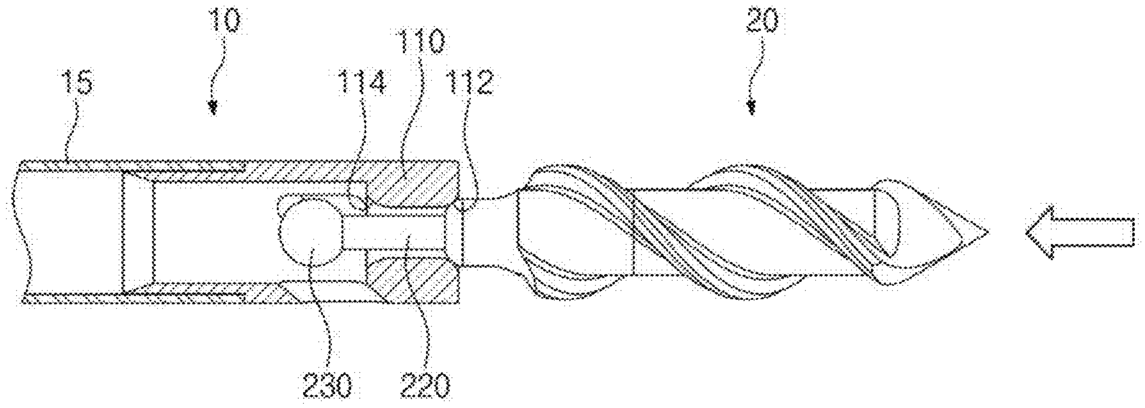
FIGS. 5 and 6 are views showing states where a position of the work member is adjusted in a forward-rearward direction with respect to a body.
Figure 6:
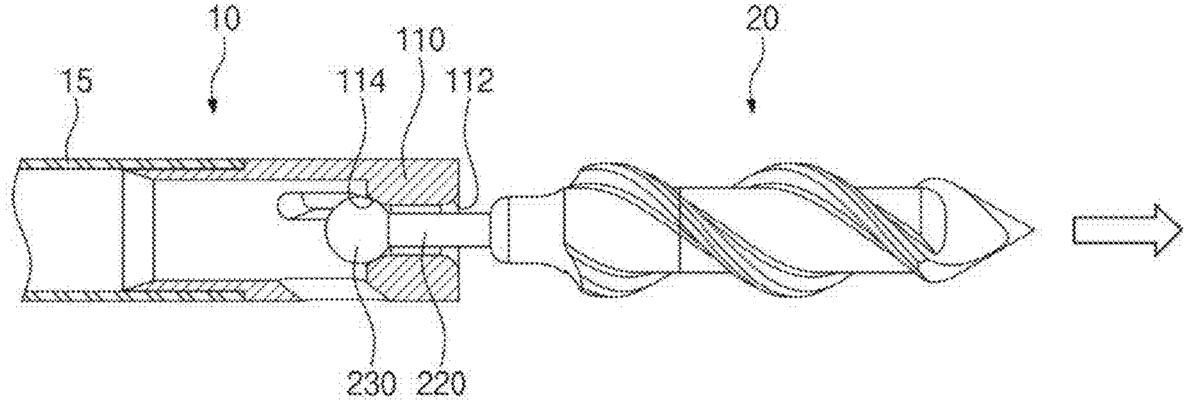

FIGS. 5 and 6 are views showing states where a position of the work member is adjusted in a forward-rearward direction with respect to a body.

Referring to FIGS. 5 and 6, the work member 20 may be provided to be movable in the forward-rearward direction with respect to the body 10. For example, when a forward-rearward position of the magnetic field applied to the work member 20 with respect to the body 10 is adjusted, the work member 20 may be moved in the forward-rearward direction with respect to the body 10 by the force applied to the work member 20 by the magnetic field. Accordingly, when the magnetic robot 1 is inserted into a blood vessel to perform a procedure, the work may be performed while moving the work member 20 in the forward-rearward direction with respect to the body 10. For example, the work member 20 may be operated in a scheme of moving in the forward-rearward direction with respect to the body 10, or in a scheme of moving in the forward-rearward direction with respect to the body 10 and rotating about the longitudinal direction of the body 10. Accordingly, a force applied to the thrombus by the work member 20 may be increased so that the thrombus may be fragmented more effectively. In addition, a work for manipulating a position of the body 10 to precisely set a forward-rearward position of the work member 20 may be omitted in the procedure using the magnetic robot 1 so that work efficiency may be increased, and a total movement distance of the body 10 and the tube 15 connected thereto in the forward-rearward direction may be reduced so that a load applied to the blood vessel may be reduced during a process of moving the body 10 and the tube 15. In addition, a position of the work member 20 with respect to the body 10 may be aligned in a process of moving the work member 20 rearward to insert the rear end of the body part 200 into the front end portion 112 of the connection part 110, so that the work member 20 may be moved in the forward-rearward direction while the position of the work member 20 with respect to the longitudinal direction of the body 10 is adjusted.

Figure 7:
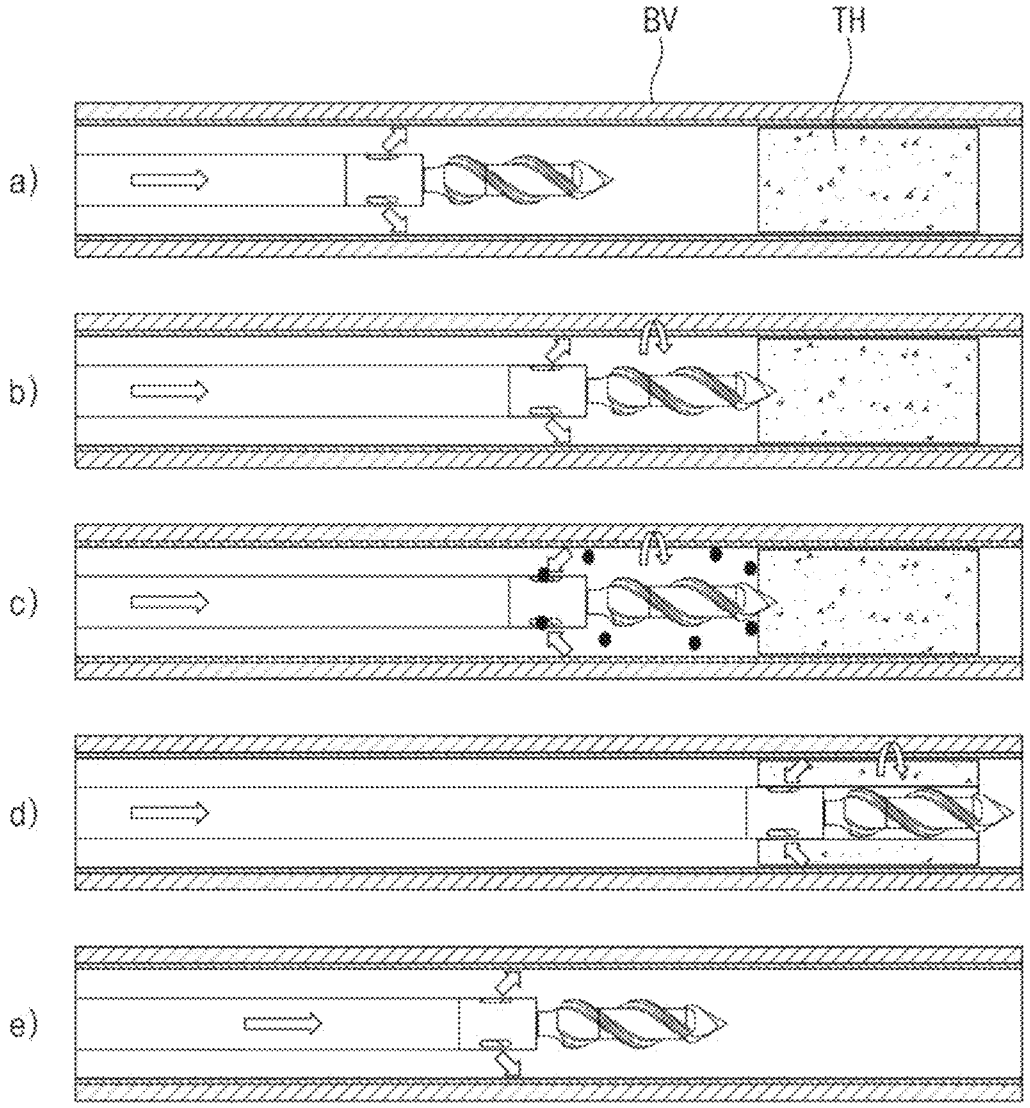
FIG. 7 is a view showing a method for inserting a magnetic robot into a blood vessel to perform a work.

FIG. 7 is a view showing a method for inserting a magnetic robot into a blood vessel to perform a work.

Referring to FIG. 7, first, the magnetic robot 1 may be moved to a region in which a thrombus TH is positioned in a blood vessel BV for a medical procedure (a). The magnetic robot 1 may be steered by a force pushing the tube 15 into the blood vessel TH, which is a force applied to the work member 20, to move through an inside of the blood vessel TH. After the magnetic robot 1 arrives at a position adjacent to the thrombus TH, or during a process of moving to a work position, a medicine may be supplied into the body 10, so that the medicine may be discharged through the communication hole 105. The medicine may be a contrast medium or a medicine used for removing a thrombus.

Thereafter, the magnetic robot 1 may move to a region in which the thrombus TH is positioned, and the work member 20 may rotate through a magnetic field, or the work member 20 may rotate while moving in the forward-rearward direction with respect to the body 10, so that the thrombus may be fragmented through a drilling work (b, c, and d). The drilling work may be performed while the body 10 is fixed or while the body 10 is moved forward. In addition, a medicine may be supplied into the body 10 during the drilling work, so that the medicine may be discharged through the communication hole 105. Accordingly, the medicine may be a medicine used for removing a thrombus. In addition, during the drilling work through the rotation of the work member 20, suction and external discharge of debris generated inside the blood vessel during the thrombus fragmenting process may be performed by suction through the communication hole 105. During the drilling work, alternation between medicine discharge and debris suction through the communication hole 105 may be performed at least once. The magnetic robot 1 may perform the drilling work by moving forward to a point where a removal target thrombus is completely fragmented by the work member 20.

Thereafter, when the fragmentation of the thrombus through the rotation of the work member 20 is completed, the magnetic robot 1 may move rearward so as to be discharged out of the blood vessel through a point where the magnetic robot 1 was first inserted into the blood vessel (e). In addition, the magnetic robot 1 may perform the medicine discharge or the debris suction through the communication hole 105 before or during the process of moving rearward after the fragmentation of the thrombus through the rotation of the work member 20.

Figure 8:
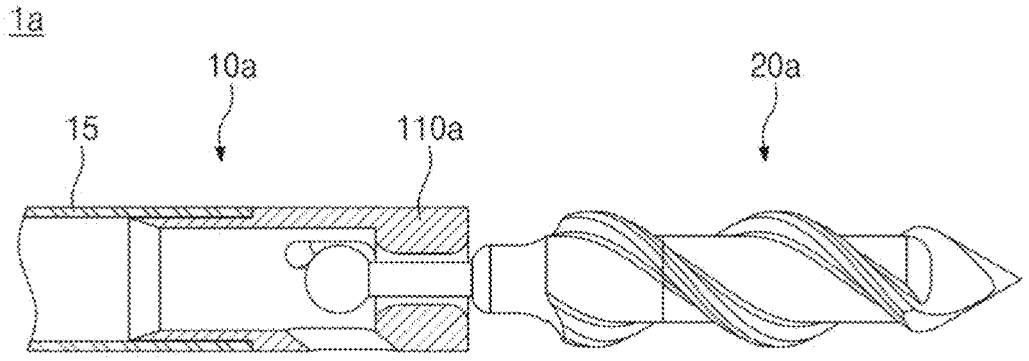
FIG. 8 is a view showing a magnetic robot according to a second embodiment of the present invention.

FIG. 8 is a view showing a magnetic robot according to a second embodiment of the present invention.

Referring to FIG. 8, a magnetic robot 1*a* may include a body 10*a* and a work member 20*a*.

The body 10*a* may include a housing part 100*a* and a connection part 110*a*.

The connection part 110*a* may be positioned at a front end portion of the housing part 100*a* so as to protrude toward a longitudinal central axis of the housing part 100*a*. Surfaces of the connection part 110*a*, which face each other in a direction perpendicular to a longitudinal direction of the housing part 100*a*, may be spaced apart from each other by a long set length, and a connection hole may be formed at an inner center of the connection part 110*a*. The connection hole may have the same area from a front end to a rear end of the connection hole.

Structures of the body 10*a* and the work member 20*a* may be identical or similar to the structures in the magnetic robot 1 of FIG. 1 except for a structure of the connection part 110*a*, so that redundant descriptions thereof will be omitted.

Figure 9:
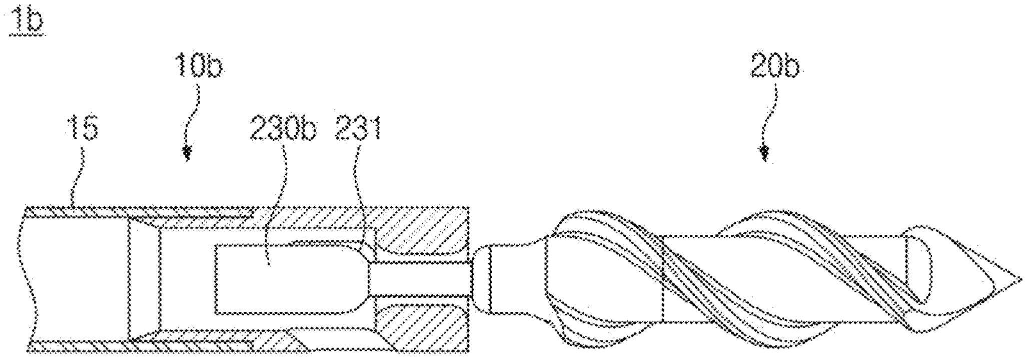
FIG. 9 is a view showing a magnetic robot according to a third embodiment of the present invention.

FIG. 9 is a view showing a magnetic robot according to a third embodiment of the present invention.

Referring to FIG. 9, a magnetic robot 1*b* may include a body 10*b* and a work member 20*b*.

At least a partial region of a separation prevention part 230*b* provided at a rear end portion of the work member 20*b* may be configured such that a section of the partial region, which is perpendicular to a longitudinal direction of the work member 20*b*, may be larger than an area of the connection hole, thereby preventing separation through the connection hole. The separation prevention part 230*b* may have a cylindrical column shape or a polygonal column shape. A front end portion 231 of the separation prevention part 230*b* may widen outward while being rounded from a front side to a rear side.

Structures of the body 10*b* and the work member 20*b* may be identical or similar to the structures in the magnetic robot 1 of FIG. 1 except for a structure of the separation prevention part 230*b*, so that redundant descriptions thereof will be omitted.

Figure 10:
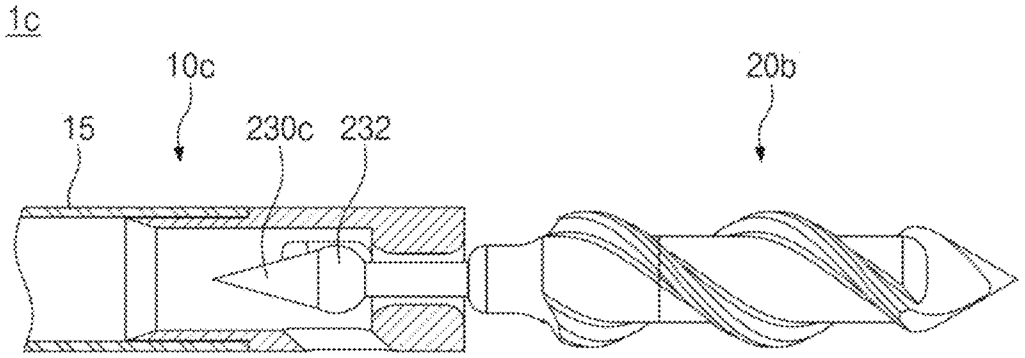
FIG. 10 is a view showing a magnetic robot according to a third embodiment of the present invention.

FIG. 10 is a view showing a magnetic robot according to a third embodiment of the present invention.

Referring to FIG. 10, a magnetic robot 1*c* may include a body 10*c* and a work member 20*c*.

At least a partial region of a separation prevention part 230*c* provided at a rear end portion of the work member 20*c* may be configured such that a section of the partial region, which is perpendicular to a longitudinal direction of the work member 20*c*, may be larger than an area of the connection hole, thereby preventing separation through the connection hole. The separation prevention part 230*c* may have a conical shape that is pointed rearward. A front end portion 232 of the separation prevention part 230*c* may widen outward while being rounded from a front side to a rear side.

Structures of the body 10*c* and the work member 20*c* may be identical or similar to the structures in the magnetic robot 1 of FIG. 1 except for a structure of the separation prevention part 230*c*, so that redundant descriptions thereof will be omitted.

Although the exemplary embodiments of the present invention have been described in detail above, the scope of the present invention is not limited to a specific embodiment, and shall be interpreted by the appended claims. In addition, it is to be understood by a person having ordinary skill in the art that various changes and modifications can be made without departing from the scope of the present invention.

INDUSTRIAL APPLICABILITY

A magnetic robot according to an embodiment of the present invention may be used to treat tubular tissues inside a body, including blood vessels.

The invention claimed is:

1. A magnetic robot comprising:

a body; and a work member connected to the body so as to be positioned in an anterior region of the body, and provided to be rotatable about a longitudinal center of the work member, wherein the body includes:

a housing part having a preset length in a forward-rearward direction so as to form an inner space; and a connection part positioned at a front end portion of the housing part so as to protrude toward a longitudinal central axis of the housing part, and having a connection hole formed at an inner center of the connection part, and wherein the work member includes:

a body part having a preset length in the forward-rearward direction, and having at least one region provided with a magnetic body;

a fastening part extending rearward from a rear end of the body part so as to be inserted into the connection hole and having a diameter smaller than a diameter of the connection hole; and a separation prevention part coupled to a rear end of the fastening part, wherein the connection hole includes:

a central region having a preset length;

a front end portion positioned at a front side of the central region, wherein the front end portion has a structure that widens outward from a rear side of the front end portion to a front side of the front end portion; and a rear end portion positioned at a rear side of the central region, wherein the rear end portion has a structure that widens outward from a front side of the rear end portion to a rear side of the rear end portion, and wherein the separation prevention part has an area larger than an area of the rear end portion.

2. The magnetic robot of claim 1, wherein a section of the connection hole, which is perpendicular to a longitudinal direction of the connection hole, has a circular shape, a section of the fastening part, which is perpendicular to a longitudinal direction of the fastening part, has a circular shape, and the diameter of the fastening part is smaller than a diameter of the central region of the connection hole by a preset length.

3. The magnetic robot of claim 1, wherein at least one communication hole is formed at an outer circumference of the housing part.

4. The magnetic robot of claim 3, wherein the communication hole is inclined forward at a preset angle from the inner space to an outside.

* * * * *